United States Patent
Park et al.

(10) Patent No.: US 10,858,379 B2
(45) Date of Patent: Dec. 8, 2020

(54) METAL PRECURSOR FOR MAKING METAL OXIDE

(71) Applicant: KOREA RESEARCH INSTITUTE OF CHEMICAL TECHNOLOGY, Daejeon (KR)

(72) Inventors: Bo Keun Park, Daejeon (KR); Taek-Mo Chung, Daejeon (KR); Dong Ju Jeon, Daejeon (KR); Jeong Hwan Han, Daejeon (KR); Ji Hyeun Nam, Incheon (KR); Chang Gyoun Kim, Daejeon (KR); Eun Ae Jung, Daegu (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 140 days.

(21) Appl. No.: 15/775,347

(22) PCT Filed: Oct. 11, 2016

(86) PCT No.: PCT/KR2016/011359
§ 371 (c)(1),
(2) Date: May 10, 2018

(87) PCT Pub. No.: WO2017/082541
PCT Pub. Date: May 18, 2017

(65) Prior Publication Data
US 2018/0334471 A1 Nov. 22, 2018

(30) Foreign Application Priority Data
Nov. 11, 2015 (KR) .................. 10-2015-0158237

(51) Int. Cl.
| | |
|---|---|
| C07F 5/00 | (2006.01) |
| C07F 7/22 | (2006.01) |
| H01L 21/02 | (2006.01) |
| C23C 16/18 | (2006.01) |
| C07C 259/06 | (2006.01) |
| C23C 16/40 | (2006.01) |
| C23C 16/455 | (2006.01) |

(52) U.S. Cl.
CPC .......... *C07F 7/2224* (2013.01); *C07C 259/06* (2013.01); *C07F 5/00* (2013.01); *C23C 16/18* (2013.01); *C23C 16/407* (2013.01); *C23C 16/45525* (2013.01); *H01L 21/0262* (2013.01); *H01L 21/02565* (2013.01)

(58) Field of Classification Search
CPC .......... C07F 7/2224; C07F 5/00; C23C 16/18; C23C 16/407; C07C 259/06
See application file for complete search history.

(56) References Cited

U.S. PATENT DOCUMENTS

| | | | | |
|---|---|---|---|---|
| 5,401,305 | A * | 3/1995 | Russo | C03C 17/2453 106/287.1 |
| 6,124,427 | A * | 9/2000 | Atwood | C01F 7/304 528/395 |
| 6,447,747 | B1 * | 9/2002 | Pirotte | A61K 51/0448 424/1.11 |
| 2003/0181745 | A1 * | 9/2003 | Shenai-Khatkhate | C07F 5/00 556/1 |
| 2003/0191333 | A1 * | 10/2003 | Shenai-Khatkhate | C07F 5/00 556/1 |
| 2007/0125998 | A1 * | 6/2007 | Bunce | B01J 8/1863 257/40 |
| 2008/0194105 | A1 * | 8/2008 | Dominguez | H01L 21/76873 438/681 |
| 2009/0203222 | A1 * | 8/2009 | Dussarrat | H01L 21/02189 438/778 |
| 2011/0262642 | A1 * | 10/2011 | Xiao | C07F 7/025 427/255.394 |
| 2012/0199794 | A1 * | 8/2012 | Stoessel | C07F 15/0033 252/301.16 |
| 2012/0231611 | A1 * | 9/2012 | Gatineau | C07D 211/12 438/478 |
| 2015/0072085 | A1 * | 3/2015 | Lansalot-Matras | C23C 16/45536 427/576 |
| 2016/0207942 | A1 * | 7/2016 | Sundermeyer | C07F 5/00 |
| 2016/0268510 | A1 * | 9/2016 | Moon | H01L 51/424 |
| 2017/0340530 | A1 * | 11/2017 | Bevacqua | A61K 8/0245 |
| 2018/0155372 | A1 * | 6/2018 | Ryu | C23C 16/407 |

FOREIGN PATENT DOCUMENTS

| | | | |
|---|---|---|---|
| CN | 1445230 A | * | 10/2003 |
| KR | 10-2010-0024558 | * | 3/2010 |
| KR | 10-2010-0024558 A | | 3/2010 |

(Continued)

OTHER PUBLICATIONS

O'Dwyer, C., et al., "Bottom-up growth of fully transparent contact layers of indium tin oxide nanowires for light-emitting devices". Nature Nanotechnology, vol. 4, Apr. 2009, pp. 239-244.*
Corneillie, Stijn, et al., "PLA architectures: the role of branching". Polym. Chem., 2015, 6, 850-867.*
Interrante, L.V., et al., Linear and Hyperbranched Polycarbosilanes with Si—CH2—Si Bridging Groups: A Synthetic Platform for the Construction of Novel Functional Polymeric Materials. Appl. Organometal. Chem. 12, 695-705 (1998).*
Darwish, Wael M., et al., "Indium(III) phthalocyanine eka-conjugated polymer as high-performance optical limiter upon nano-second laser irradiation". High Performance Polymers, 2016, vol. 28 (6) 651-659.*

(Continued)

*Primary Examiner* — Bret P Chen
(74) *Attorney, Agent, or Firm* — Knobbe Martens Olson & Bear LLP

(57) ABSTRACT

A novel metal precursor having improved thermal stability and volatility is provided. Also provided herein are: a method for readily manufacturing a good quality metal oxide thin film at an excellent growth rate at low temperature by using the metal precursor; and a thin film manufactured by using the same.

4 Claims, 2 Drawing Sheets

(56) References Cited

FOREIGN PATENT DOCUMENTS

KR   10-2012-0125102 A      11/2012
KR          101530043 B1 *  6/2015

OTHER PUBLICATIONS

Graisa et al., "Organotin(IV) Derivatives of N-Tolyl-m-methoxybenzohydroxamic Acid: Synthesis and Structural Elucidation", International Journal of Chemistry, vol. 1, No. 2—14 pages, (Aug. 2009).

Harrison et al., "Structural Studies in Main Group Chemistry, XXVI* . The Structure of o-trimethylstannyl-N-phenyl-N-benzoylhydroxylamine", Journal of Organometallic Chemistry, vol. 185—10 pages, (1980).

Das et al., "Di- and Triorganotin(IV) Derivatives of N,N-Substituted Hydroxylamines", Inorganica Chimica Acta, vol. 71—11 pages, (1983).

Shang et al, "New Coordination Modes of Substituted Benzohydroxamic Acid with Dialkyltin(IV): Structural Diversity through Ligand Isomerization", European Journal of Inorganic Chemistry—8 pages. (2006).

International Search Report of PCT/KR2016/011359 which is the parent application and its English translation—6 pages, (Feb. 20, 2017).

* cited by examiner

METAL PRECURSOR FOR MAKING METAL OXIDE

TECHNICAL FIELD

The present invention relates to a novel metal precursor, and more particularly, to a metal precursor having improved thermal stability and volatility and being capable of readily manufacturing a high quality metal oxide thin film at a low temperature, a manufacturing method therefor, and a method for manufacturing a thin film using the same, and a thin film manufactured therefrom.

BACKGROUND ART

Silicon is advantageous in view of physical properties, lifetime, and performance stability. However, to form a thin film, vacuum deposition and annealing, etc., are required, and high-priced equipment for the required processes increases display production costs. In this regard, efforts are recently being made to use a metal oxide material as a semiconductor channel layer, wherein metal oxide has the potential as a material for transparent device.

An oxide semiconductor has higher electron mobility than amorphous silicon, is easier to be processed at a low temperature than polycrystalline silicon, and is transparent in a visible light region, and thus has been researched as a semiconductor layer of an electronic device such as a thin film transistor.

As the oxide semiconductor, materials in which various kinds of metal atoms are added while including indium (In), zinc (Zn), or the like as a base material, have been used. A thin film of the oxide semiconductor is mainly manufactured by processes such as PLD (pulsed laser deposition), sputtering, ALD (atomic layer deposition), etc.

In particular, since indium (In) oxide is transparent and maintains high conductivity, a number of researches thereof have been conducted as a transparent electrode material such as a transistor electrode and a touch screen, or the like. Chemical vapor deposition (CVD), atomic layer deposition (ALD), or the like, has been used as a process for forming an oxide thin film including indium as a base material.

Meanwhile, a tin (Sn) oxide semiconductor receives attention since it is capable of replacing an oxide semiconductor including indium. Chemical vapor deposition (CVD), atomic layer deposition (ALD), or the like, has been used as a process for forming an oxide thin film including tin as a base material.

However, when a tin oxide thin film or an indium oxide thin film is manufactured by the CVD or ALD process as described above, it is necessary to develop a metal precursor having excellent characteristics since a degree of deposition, a deposition control characteristic, crystallinity and purity of the oxide thin film to be formed, etc., differ depending on the characteristics of the metal precursor to be used.

In addition, researches on synthesis of tin or indium precursor usable for the semiconductor channel layer are insufficient, and development of a precursor in which thermal stability, chemical reactivity, volatility, and deposition rate of tin or indium metal is improved is urgently required.

DISCLOSURE

Technical Problem

The present invention has been made to solve the above problems.

An object of the present invention is to provide a novel metal precursor having improved thermal stability and volatility and being capable of readily manufacturing a high quality metal oxide thin film at a low temperature.

Another object of the present invention is to provide a novel method for manufacturing the metal precursor, a method for manufacturing a metal oxide thin film using the same, and a metal oxide thin film manufactured therefrom.

Technical Solution

In one general aspect, there is provided a metal precursor represented by Chemical Formula 1 below:

[Chemical Formula 1]

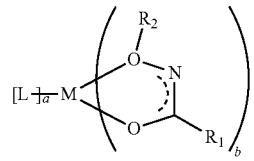

in Chemical Formula 1, $R_1$ and $R_2$ are each independently a C1 to C10 linear or branched alkyl group; M is indium (III) or tin (II); L is a C1 to C4 linear or branched alkyl group; and a is an integer of 0 or 2, b is an integer of 1 or 2, and a+b indicating an oxidation number of M is an integer of 2 or 3.

In another general aspect, there is provided a method for manufacturing a metal precursor represented by Chemical Formula 2 below by reacting an N-alkoxy alkylamide ligand represented by Chemical Formula 4 below with an indium compound represented by Chemical Formula 5 below:

[Chemical Formula 2]

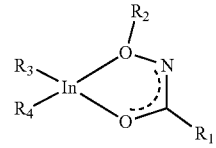

[Chemical Formula 4]

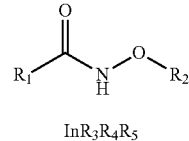

[Chemical Formula 5]

$InR_3R_4R_5$ in Chemical Formulas 2, 4 and 5, $R_1$ and $R_2$ are each independently a C1 to C10 linear or branched alkyl group, and $R_3$, $R_4$, and $R_5$ are each independently a C1 to C4 linear or branched alkyl group.

In still another general aspect, there is provided a method for manufacturing a metal precursor represented by Chemical Formula 3 below by reacting an N-alkoxy alkylamide ligand represented by Chemical Formula 4 below with tin(di-bistrimethylsilylamide) $(Sn(btsa)_2)$:

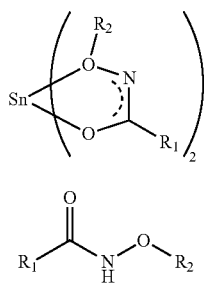
[Chemical Formula 3]

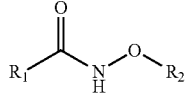
[Chemical Formula 4]

in Chemical Formulas 3 and 4, $R_1$ and $R_2$ are each independently a C1 to C10 linear or branched alkyl group.

In still another general aspect, there are provided a method for growing a metal oxide thin film using the metal precursor as described above, and a metal oxide thin film manufactured therefrom.

Advantageous Effects

Since the metal precursor of the present invention includes an N-alkoxyalkylamide ligand and has improved thermal stability and improved volatility, the high quality metal oxide thin film, particularly, an indium oxide thin film or a tin oxide thin film, is able to be readily manufactured by using the same.

BEST MODE

Figure 1:
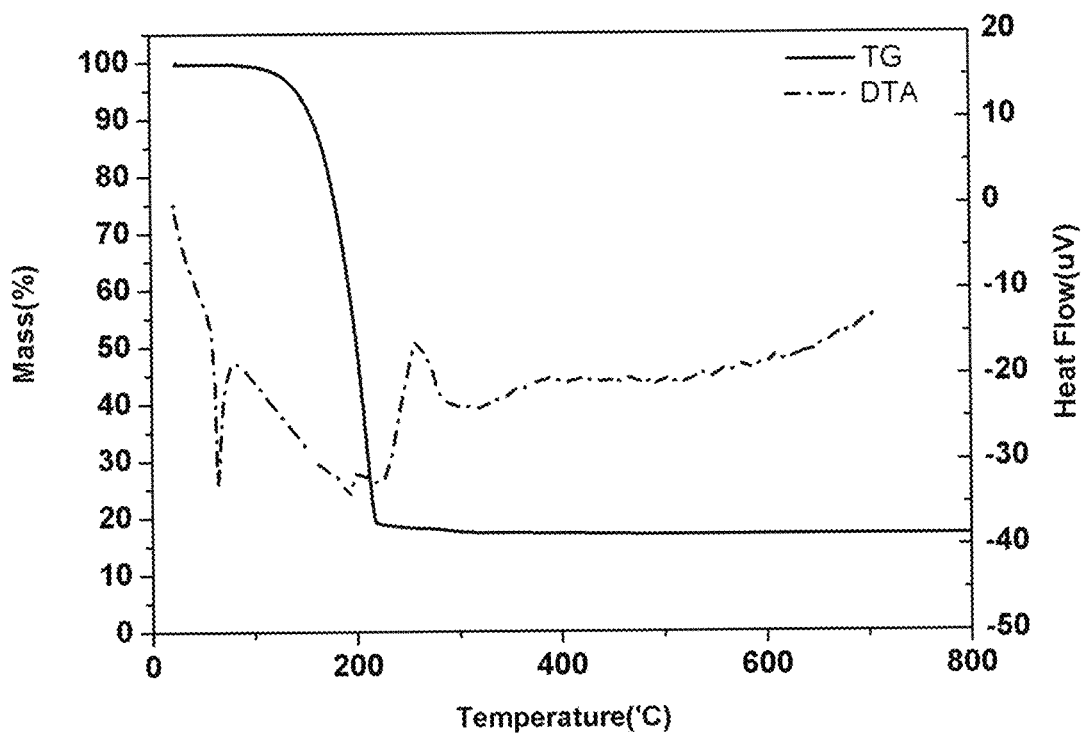
FIG. 1 is TG data of $In(CH_3)_2$(N-methoxypropanamide).

Hereinafter, the present invention will be described in detail. Here, unless technical and scientific terms used herein are defined otherwise, they have meanings understood by those skilled in the art to which the present invention pertains. Known functions and components which obscure the description and the accompanying drawings of the present invention with unnecessary detail will be omitted.

The present invention relates to a metal precursor represented by Chemical Formula 1 below.

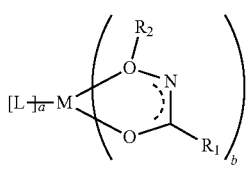
[Chemical Formula 1]

in Chemical Formula 1, $R_1$ and $R_2$ are each independently a C1 to C10 linear or branched alkyl group; M is indium (III) or tin (II); L is a C1 to C4 linear or branched alkyl group; and a is an integer of 0 or 2, b is an integer of 1 or 2, and a+b indicating an oxidation number of M is an integer of 2 or 3.

The metal precursor may be an indium precursor represented by Chemical Formula 2 below or a tin precursor represented by Chemical Formula 3 below:

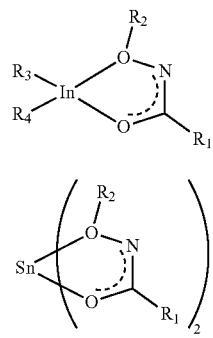
[Chemical Formula 2]

[Chemical Formula 3]

in Chemical Formulas 2 and 3, $R_1$ and $R_2$ are each independently a C1 to C10 linear or branched alkyl group; and $R_3$ and $R_4$ are each independently a C1 to C4 linear or branched alkyl group.

More preferably, in Chemical Formula 2, $R_1$, $R_2$, $R_3$ and $R_4$ may be each independently methyl, ethyl, propyl, iso-propyl, butyl, iso-butyl, or tert-butyl, and in Chemical Formula 3, $R_1$ and $R_2$ may be each independently methyl, ethyl, propyl, iso-propyl, butyl, iso-butyl or tert-butyl.

The metal precursor represented by Formula 1 is a novel compound having excellent thermal stability and improved volatility. In addition, when the metal precursor is used to manufacture a thin film, it is possible to manufacture a thin film at a relatively low temperature with an excellent growth rate.

The indium precursor represented by Chemical Formula 2 may be prepared by reacting an N-alkoxy alkylamide ligand represented by Chemical Formula 4 below and an indium compound represented by Chemical Formula 5 below as starting materials in an organic solvent to induce a substitution reaction:

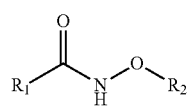
[Chemical Formula 4]

[Chemical Formula 5]

in Chemical Formulas 4 and 5 below, $R_1$ and $R_2$ are each independently a C1 to C10 linear or branched alkyl group, and $R_3$, $R_4$, and $R_5$ are each independently a C1 to C4 linear or branched alkyl group.

Examples of the organic solvent used in the reaction may include, but are not limited to, hexane, diethylether, toluene, tetrahydrofuran (THF), etc. Preferably, toluene may be used.

A method for preparing the indium precursor of the present invention may be represented by Reaction Scheme 1 below:

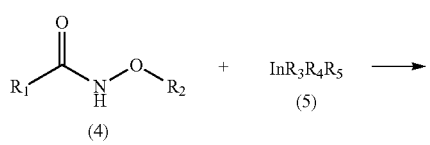
[Reaction Scheme 1]

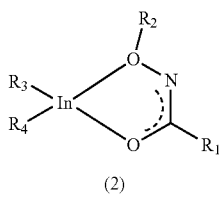

(2)

in Reaction Scheme 1, $R_1$ and $R_2$ are each independently a C1 to C10 linear or branched alkyl group, and $R_3$, $R_4$, and $R_5$ are each independently a C1 to C4 linear or branched alkyl group.

According to Reaction Scheme 1, the reaction may be performed preferably by raising a low temperature that is lower than 0° C. to room temperature (rt), for 10 to 24 hours, in a solvent such as hexane, diethyl ether, toluene or tetrahydrofuran. Thus, the compound represented by Chemical Formula 2, which is a solid or a liquid, may be obtained. In addition, by-products may be obtained during the reaction of Reaction Scheme 1, and may be removed under reduced pressure, thereby obtaining a novel indium precursor (Chemical Formula 2) with high purity.

Reactants in the above reaction may be used in a stoichiometric equivalent ratio.

The tin precursor represented by Chemical Formula 3 may be prepared by reacting an N-alkoxy alkylamide ligand represented by Chemical Formula 4 below and Sn(btsa)$_2$ (btsa=bistrimethylsilylamine) as starting materials in an organic solvent to induce a substitution reaction:

[Chemical Formula 4]

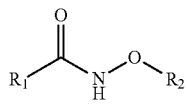

in Chemical Formula 4, $R_1$ and $R_2$ are each independently a C1 to C10 linear or branched alkyl group.

Examples of the organic solvent used in the reaction may include, but are not limited to, hexane, diethylether, toluene, tetrahydrofuran (THF), and dichloromethane (MC), etc. Preferably, tetrahydrofuran (THF) or dichloromethane (MC) may be used.

A method for preparing the tin precursor of the present invention may be represented by Reaction Scheme 2 below:

[Reaction Scheme 2]

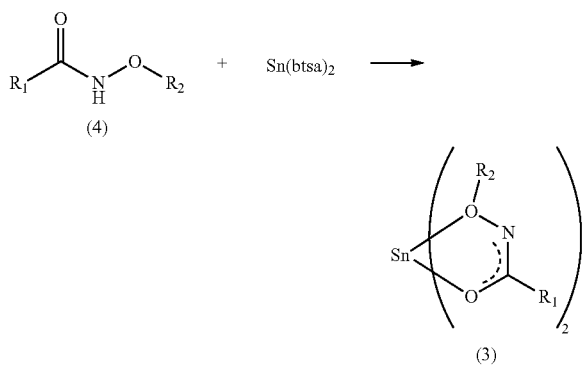

in Reaction Scheme 2, $R_1$ and $R_2$ are each independently a C1 to C10 linear or branched alkyl group.

According to Reaction Scheme 2, the reaction may be performed in a solvent such as hexane, diethyl ether, toluene, dichloromethane or tetrahydrofuran, preferably at room temperature (rt) for 12 to 24 hours. Thus, the compound represented by Chemical Formula 3, which is a solid or a liquid, may be obtained. In addition, by-products may be obtained during the reaction of Reaction Scheme 2, and may be removed by using sublimation, distillation, or the like, thereby obtaining a novel tin precursor (Chemical Formula 3) with high purity.

Reactants in the above reaction may be used in a stoichiometric equivalent ratio.

The metal precursor of the present invention may be a white solid or a transparent liquid at room temperature, and is thermally stable and has good volatility.

In particular, when an indium oxide thin film is grown by using the indium precursor represented by Chemical Formula 2, the thin film may be readily manufactured at a low temperature.

In addition, when the tin oxide thin film is grown by using the tin precursor represented by Chemical Formula 3, the thin film may be readily manufactured at a low temperature with a good growth rate.

The novel metal precursor of the present invention is a precursor for preparing a metal oxide thin film, and particularly, may be preferably applied to a process using chemical vapor deposition (CVD) or atomic layer deposition (ALD).

For example, when the chemical vapor deposition (CVD) is used, the metal oxide thin film may be formed on various substrates by supplying reactants including the metal precursor of the present invention, and organic materials, etc., to a reactor. Since the novel metal precursor of the present invention is thermally stable and has good volatility, it is possible to manufacture a thin film under various conditions and to manufacture a good quality thin film.

Further, for example, when the atomic layer deposition (ALD) is used, the metal oxide thin film may be manufactured by the ALD process using the metal precursor of the present invention. In the ALD process, reactants including the metal precursor of the present invention are pulsed into a deposition chamber, and the pulse is chemically reacted with a wafer surface to achieve precise monolayer film growth. Since the metal precursor of the present invention is thermally stable and has good volatility, the high quality metal oxide thin film may be readily manufactured by the ALD process.

The present invention will be more appreciated by the following Examples, which are given by way of illustration but are not intended to limit the protective scope defined by the attached claims of the present invention.

SYNTHESIS EXAMPLE

Synthesis Example 1 Synthesis of N-methoxy-2,2-dimethyl propanamide (MDPA)

O-Methylhydroxylamine hydrochloride (1.5 g, 1.1 eq) and 50 mL of tetrahydrofuran (THF) were placed in a round-bottom flask and stirred at 70° C. for 12 hours. At 0° C., triethylamine (7 mL, 3 eq) was added thereto, a temperature was raised up to room temperature, and the mixture was stirred for 30 minutes. Then, pivaloyl chloride (2 g, 1 eq) was slowly added dropwise and reacted at 70° C. for 24 hours. After 24 hours, the mixture was filtered using ethyl acetate (EA), concentrated under reduced pressure, and then washed with EA. The thus-obtained mixture was purified by column chromatography (EA:Hex=1:1 to EA conversion) to obtain N-methoxy-2,2-dimethyl propanamide as transparent crystals (1.2 g, 56%).

$^1$H NMR ($C_6D_6$, 400 MHz) δ 1.09 (s, 9H, COC(CH$_3$)$_3$), 3.59 (s, 3H, OCH$_3$), 9.30 (s, 1H, NH).

$^{13}$C NMR ($C_6D_6$, 100 MHz) δ 27.2 (COC(CH$_3$)$_3$), 37.8 (COC(CH$_3$)$_3$) 63.5 (OCH$_3$), 175.8 (COC(CH$_3$)$_3$).

FT-IR ($v_{max}$, cm$^{-1}$) 3228s, 2967s, 2873m, 2813m, 2813w, 1653s, 1506s, 1482s, 1440w, 1400m, 1368 m, 1294w, 1226m, 1060s, 1021m, 941m, 917m, 811w, 622w, 586w.

Anal. Calcd for $C_6H_{13}NO_2$: C, 54.94; H, 9.99; N, 10.68. Found: C, 54.45; H, 9.87; N, 10.42.

EI-MS (m/z): 131 (M$^+$)

Synthesis Example 2. Synthesis of
N-ethoxy-2,2-dimethyl propanamide (EDPA)

O-Ethylhydroxylamine hydrochloride (10.1 g, 1.1 eq) and 130 mL of tetrahydrofuran (THF) were placed in a round-bottom flask and stirred at 70° C. for 12 hours. At 0° C., triethylamine (42 mL, 3 eq) was added thereto, a temperature was raised up to room temperature, and the mixture was stirred for 30 minutes. Then, pivaloyl chloride (12 g, 1 eq) was slowly added dropwise and reacted at 70° C. for 24 hours. After 24 hours, the mixture was filtered through ethyl acetate (EA), concentrated under reduced pressure, and distilled under reduced pressure to obtain a viscous and transparent liquid, N-ethoxy-2,2-dimethyl propanamide (10 g, 69%).

$^1$H NMR ($C_6D_6$, 400 MHz) δ 1.10 (s, 9H, COC(CH$_3$)$_3$, 1.16 (t, 3H, OCH$_2$CH$_3$), 3.84 (q, 2H, OCH$_2$CH$_3$), 8.20 (s, 1H, NH).

$^{13}$C NMR ($C_6D_6$, 100 MHz) δ 13.7 (OCH$_2$CH$_3$), 27.4 (COC(CH$_3$)$_3$), 37.9 (COC(CH$_3$)$_3$), 71.4 (OCH$_2$CH$_3$), 176.0 (COC(CH$_3$)$_3$).

FT-IR ($v_{max}$/cm$^{-1}$): 3226s, 2979s, 1652s, 1506s, 1483s, 1462m, 1399w, 1386w, 1368w, 1294w, 1229w, 1159w, 1123w, 1091w, 1057s, 1029m, 1009m, 933m, 863w, 812w, 598w.

Anal. Calcd for $C_7H_{15}NO_2$: C, 57.90; H, 10.41; N, 9.65. Found: C, 57.88; H, 10.38; N, 9.61.

EI-MS (m/z): 145 (M$^+$)

<Example> Synthesis of Indium Precursor Material

Example 1. Preparation of In(CH$_3$)$_2$ (N-methoxy propanamide)

In an Erlenmeyer flask, In(CH$_3$)$_2$ (1.0 g, 6.25 mmol) and 75 mL of toluene were added and dissolved. N-Methoxy-propanamide (0.64 g, 6.25 mmol) was added thereto at −78° C., the temperature was raised to room temperature, and the mixture was stirred for 12 hours. The reaction product was filtered, and the resulting solution was decompressed to remove by-products. Then, after the mixture was extracted with hexane and the hexane was removed, the mixture was dried to obtain a white solid compound. The obtained white solid compound was purified by sublimation at 60 to 70° C./0.05 mmHg to obtain a pure compound (0.82 g, yield of 82%), wherein a melting point was 73° C.

$^1$H NMR ($C_6D_6$, 300 MHz): δ 0.07 (s, 6H, (CH$_3$)$_2$In), 1.10 (t, 3H, COCH$_2$CH$_3$), 2.10 (q, 2H, COCH$_2$CH$_3$), 3.45 (s, 3H, OCH$_3$).

$^{13}$C NMR ($C_6D_6$, 75 MHz): δ −4.12 ((CH$_3$)$_2$In), 10.55 (COCH$_2$CH$_3$), 27.18 (COCH$_2$CH$_3$), 59.81 (OCH$_3$), 163.86 (COCH$_2$CH$_3$).

FT-IR ($v_{max}$/cm$^{-1}$): 2981m, 2941m, 2914m, 2826w, 1609s, 1453w, 1426w, 1375s, 1366s, 1268s, 1197m, 1160w, 1051s, 1020m, 931w, 868m, 800w, 723m, 619m, 535m, 487w, 463m.

Anal. Calcd for $C6H_{14}NO_2In$: C, 29.18; H, 5.71; N, 5.67. Found: C, 29.42; H, 5.80, N; 5.58.

Example 2. Preparation of In(CH$_3$)$_2$(N-ethoxy-2,2-dimethyl propanamide)

In an Erlenmeyer flask, In(CH$_3$)$_2$ (1.0 g, 6.25 mmol) and 75 mL of toluene were added and dissolved. N-Ethoxy-2,2-dimethyl propanamide (0.90 g, 6.25 mmol) was added thereto at −78° C., the temperature was raised to room temperature, and the mixture was stirred for 12 hours. The reaction product was filtered, and the resulting solution was decompressed to remove by-products. Then, after the mixture was extracted with hexane and the hexane was removed, the mixture was dried to obtain a colorless liquid compound. The thus-obtained colorless liquid compound was purified at 90 to 100° C./0.05 mmHg to obtain a pure compound (0.68 g, yield 68%).

$^1$H NMR ($C_6D_6$, 300 MHz): δ 0.14 (s, 6H, (CH$_3$)$_2$In), 1.06 (t, 3H, OCH$_2$CH$_3$), 1.26 (s, 9H, COC(CH$_3$)$_3$), 3.84 (q, 2H, OCH$_2$CH$_3$).

$^{13}$C NMR ($C_6D_6$, 75 MHz): δ −2.72 ((CH$_3$)$_2$In), 14.98 (OCH$_2$CH$_3$), 28.19 (COC(CH$_3$) 3), 36.46 (COC(CH$_3$) 3), 68.67 (OCH$_2$CH$_3$), 168.30 (COC(CH$_3$)$_3$).

FT-IR ($v_{max}$/cm$^{-1}$) 2974s, 2930s, 2871s, 1585s, 1479s, 1459s, 1394s, 1382m, 1360m, 1318s, 1219w, 1183s, 1125m, 1090s, 1052s, 959m, 934w, 912s, 898s, 864s, 786m, 723s, 589s, 532s, 484m, 454m, 437m, 409w.

Anal. Calcd for $C_9H_{20}NO_2In$: C, 37.39; H, 6.97; N, 4.85. Found: C, 36.88; H, 7.01; N, 4.61.

EI-MS (m/z): 289 (M$^+$)

EXPERIMENTAL EXAMPLE

Experimental Example 1. Analysis of Indium Precursor Material

Thermogravimetric analysis (TGA) was used to measure thermal stability, volatility and decomposition temperature of In(CH$_3$)$_2$(N-methoxy propanamide) of Example 1 and In(CH$_3$)$_2$(N-ethoxy-2,2-dimethyl propanamide of Example 2. In the TGA method, argon gas was introduced at a pressure of 1.5 bar/min while heating the product up to 800° C. at a rate of 10° C./minute.

It was observed that the indium precursor compound of Example 1 began to have a mass reduction near 100° C. and a mass reduction of about 82% or more at 225° C. [FIG. 1].

Figure 2:
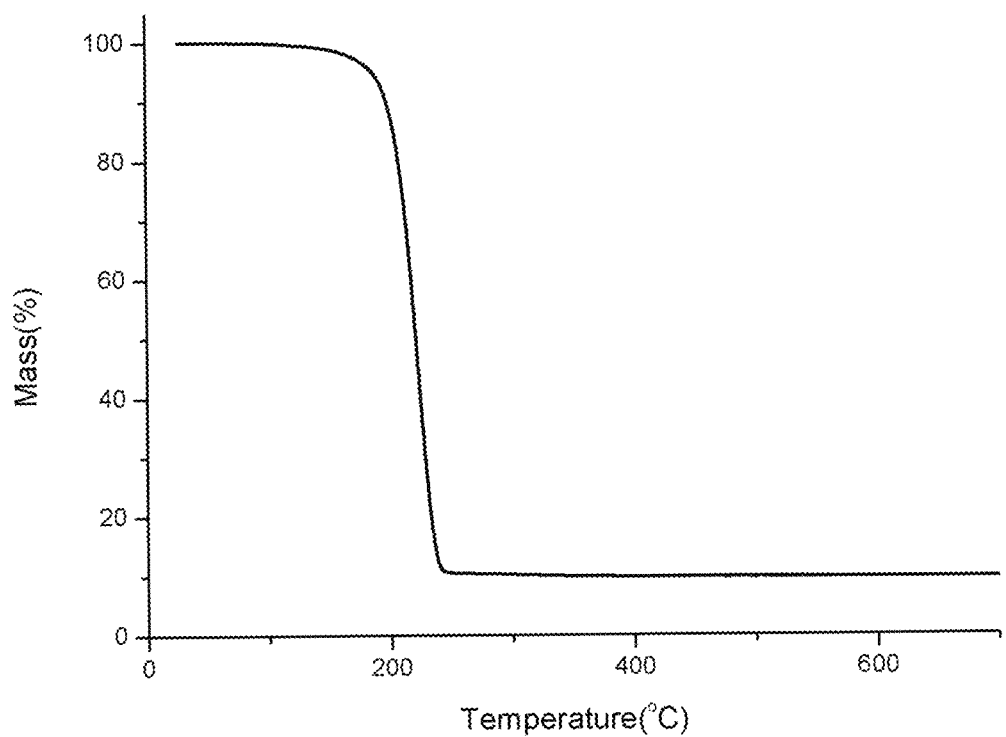
FIG. 2 is TG data of $In(CH_3)_2$(N-ethoxy-2,2-dimethyl propanamide).

It was observed that the indium precursor compound of Example 2 began to have a mass reduction near 150° C. and a mass reduction of about 90% or more at 243° C. [FIG. 2].

In addition, the TGA data show that a degree of volatility of the compound of the present invention is very good.

<Example> Synthesis of Tin Precursor Material

Example 3. Preparation of Sn(MDPA)$_2$

Sn(btsa)$_2$ (0.84 g, 0.5 eq) and 5 mL of hexane were stirred. MDPA (0.5 g, 1 eq) prepared in Synthesis Example 1 and 5 mL of hexane were mixed, and then added dropwise to the mixture of Sn(btsa)$_2$ and hexane at 0° C. When the solution became gradually transparent, the reaction was reacted at room temperature for 12 hours. When formation of the solid was visually confirmed, the solution was concentrated under reduced pressure and sublimated at 60° C./10-1 torr to obtain a target compound of Sn(MDPA)$_2$ (0.2 g, 29%) as a white solid.

$^1$H NMR (C$_6$D$_6$, 400 MHz) δ 1.32 (s, 9H, COC(CH$_3$)$_3$), 3.67 (s, 3H, OCH$_3$).

$^{13}$C NMR (C$_6$D$_6$, 100 MHz) δ 28.3 (COC(CH$_3$)$_3$), 36.0 (COC(CH$_3$)$_3$), 59.6 (OCH$_3$), 172.1 (COC(CH$_3$)$_3$).

FT-IR (ν$_{max}$/cm$^{-1}$): 2970m, 2957m, 2904w, 2865w, 1579s, 1480m, 1437w, 1421w, 1395w, 1358w, 1324m, 1224w, 1188s, 1028s, 931m, 844m, 785w, 734w, 599m, 527w, 467m.

Anal. Calcd for C$_{12}$H$_{24}$N$_2$O$_4$Sn: C, 38.28; H, 7.36; N, 7.37. Found: C, 38.03; H, 7.29; N, 7.32.

EI-MS (m/z): 380 (M$^+$)

Example 4. Preparation of Sn(EDPA)$_2$

Sn(btsa)$_2$ (0.8 g, 0.5 eq) and 10 mL of diethylether were stirred. EDPA (0.5 g, 1 eq) prepared in Synthesis Example 2 and 10 mL of diethylether were mixed, and then added dropwise to the mixture of Sn(btsa)$_2$ and diethylether. When the solution became gradually transparent, the reaction was reacted at room temperature for 24 hours. Then, the mixture was concentrated under reduced pressure, followed by distillation under reduced pressure at 90° C./10-1 torr to obtain a target compound of Sn(EDPA)$_2$ (0.24 g/34%) as a transparent liquid.

$^1$H NMR (C$_6$D$_6$, 400 MHz) δ 1.25 (t, 3H, OCH$_2$CH$_3$), 1.33 (s, 9H, COC(CH$_3$)$_3$), 4.15 (q, 2H, OCH$_2$CH$_3$).

$^{13}$C NMR (C$_6$D$_6$, 100 MHz) δ 15.7 (OCH$_2$CH$_3$), 28.3 (COC(CH$_3$) 3), 36.2 (COC(CH$_3$) 3), 69.5 (OCH$_2$CH$_3$), 171.5 (COC(CH$_3$)$_3$).

FT-IR (ν$_{max}$/cm$^{-1}$): 2976s, 2902w, 2870w, 1581s, 1481m, 1457w, 1393m, 1358w, 1330s, 1197s, 1122w, 1092w, 1044s, 960w, 937w, 899w, 852w, 789w, 775w, 733w, 605m, 509w, 467w.

Anal. Calcd for C$_{14}$H$_{28}$N$_2$O$_4$Sn: C, 41.31; H, 6.90; N, 6.88. Found: C, 41.13; H, 6.88; N, 6.75.

EI-MS (m/z): 408 (M$^+$)

EXPERIMENTAL EXAMPLE

Experimental Example 2. Analysis of Tin Precursor Material

Figure 3:
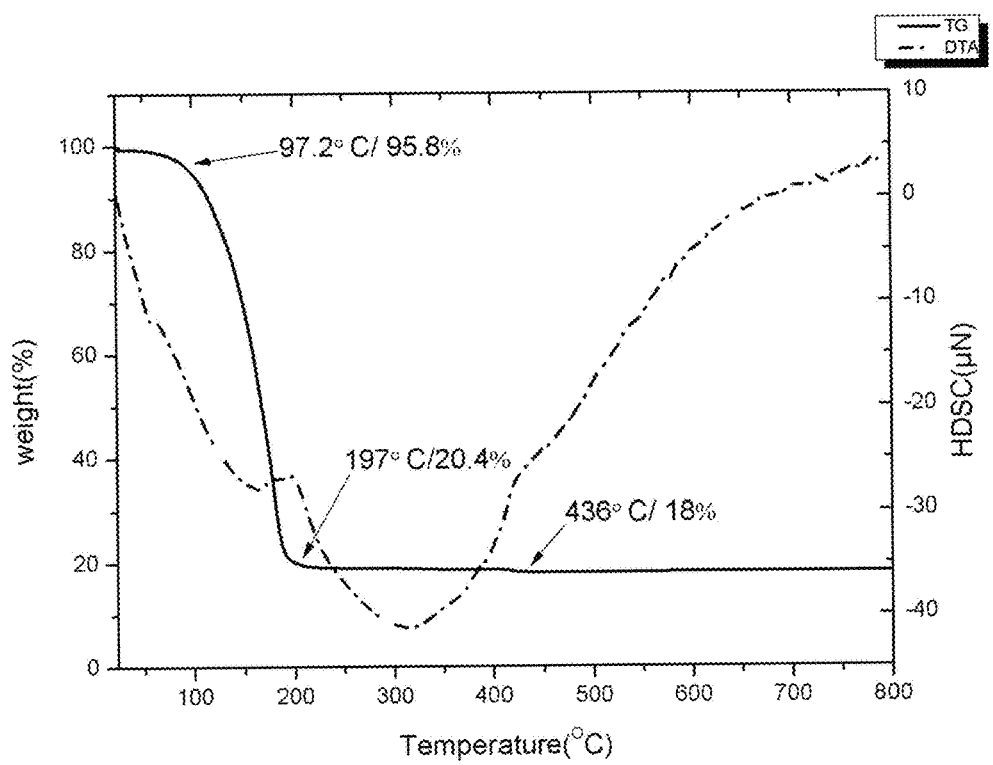
FIG. 3 is TG/DTA data for $Sn(MDPA)_2$.
Figure 4:
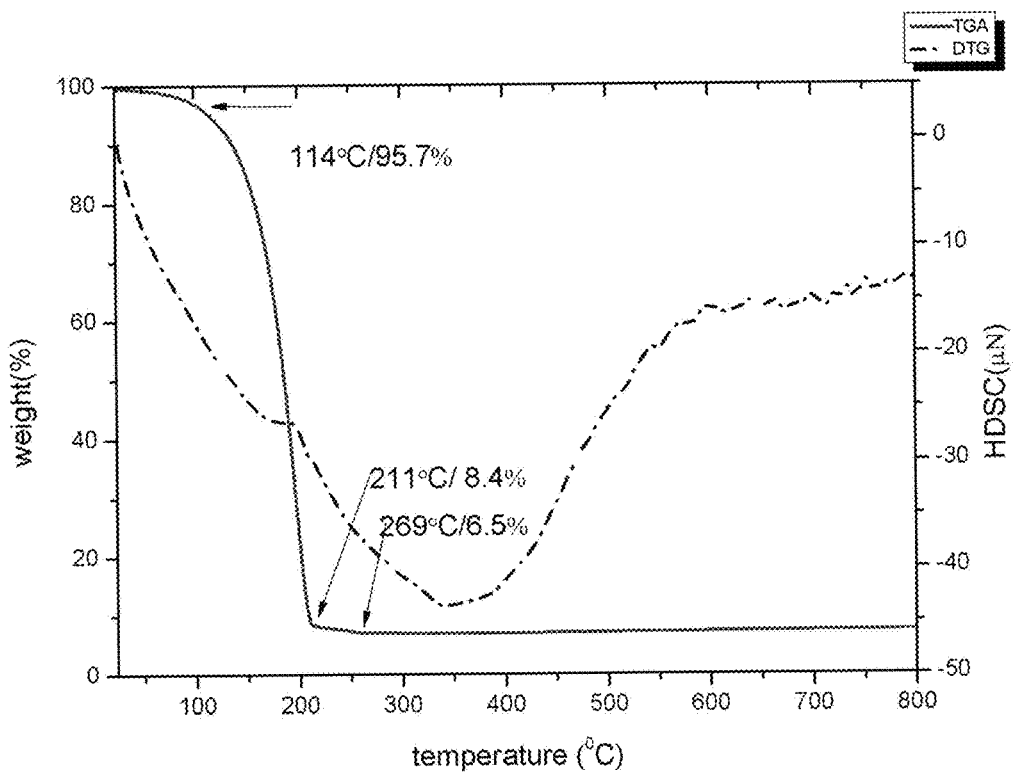
FIG. 4 is TG/DTA data for $Sn(EDPA)_2$.

Thermogravimetric analysis (TGA) was used to measure thermal stability, volatility and decomposition temperature of Sn(MDPA)$_2$ of Example 3 and Sn(EDPA)$_2$ of Example 4. In the TGA method, argon gas was introduced at a pressure of 1.5 bar/min while heating the product up to 800° C. at a rate of 10° C./minute. A TGA graph of the tin precursor compound synthesized in Example 3 is shown in FIG. 3, and a TGA graph of the tin precursor compound synthesized in Example 4 is shown in FIG. 4. As could be appreciated from FIG. 3, the tin precursor compound of Example 3 began to have a mass reduction from 100° C. and had a final residual amount of 18% observed at 436° C. In addition, as could be appreciated from FIG. 4, the tin precursor compound of Example 4 began to have a mass reduction from 114° C. and had a final residual amount of 6.4% observed at 269° C.

In addition, the TGA data show that a degree of volatility of the compound of the present invention is very good.

INDUSTRIAL APPLICABILITY

Since the metal precursor of the present invention includes an N-alkoxyalkylamide ligand and has improved thermal stability and improved volatility, the high quality metal oxide thin film, particularly, an indium oxide thin film or a tin oxide thin film, is able to be readily manufactured by using the same.

The invention claimed is:

1. A metal precursor represented by Chemical Formula 1 below:

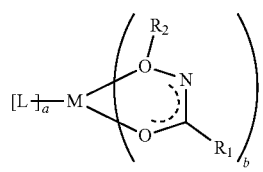

[Chemical Formula 1]

wherein in Chemical Formula 1,
R$_1$ and R$_2$ are each independently a C1 to C10 linear or branched alkyl group;
M is indium (III) or tin (II);
L is a C1 to C4 linear or branched alkyl group; and
a is an integer of 0 or 2, b is an integer of 1 or 2, and a+b indicating an oxidation number of M is an integer of 2 or 3,
wherein the metal precursor is represented by Chemical Formula (2) or (3) below:

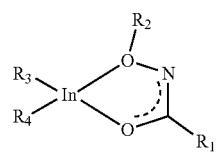

[Chemical Formula 2]

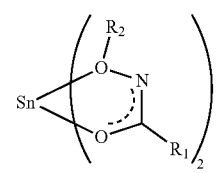

[Chemical Formula 3]

wherein in Chemical Formulas 2 and 3, R$_1$ and R$_2$ are each independently a C1 to C10 linear or branched alkyl group; and R$_3$ and R$_4$ are each independently a C1 to C4 linear or branched alkyl group.

2. The metal precursor of claim 1, wherein R$_1$, R$_2$, R$_3$ and R$_4$ are each independently selected from the group consisting of methyl, ethyl, propyl, iso-propyl, butyl, iso-butyl, or tert-butyl.

3. A method for growing a metal oxide thin film using the metal precursor of claim 1.

4. The method of claim 3, wherein a thin film growth process is performed by chemical vapor deposition (CVD) or atomic layer deposition (ALD).

* * * * *